(12) United States Patent
Muessig et al.

(10) Patent No.: US 11,497,922 B2
(45) Date of Patent: Nov. 15, 2022

(54) MODULAR CONNECTOR HOUSING CONCEPT

(71) Applicant: BIOTRONIK SE & CO. KG, Berlin (DE)

(72) Inventors: Dirk Muessig, West Linn, OR (US);
Matthew Melius, Portland, OR (US);
Eric Austin, Portland, OR (US);
Andreas Becker, Wilsonville, OR (US);
Alan Fryer, Portland, OR (US);
Torsten Oertmann, Blankenfelde (DE);
Rolf Klenner, Michendorf (DE)

(73) Assignee: BIOTRONIK SE & Co. KG, Berlin (DE)

( * ) Notice: Subject to any disclaimer, the term of this patent is extended or adjusted under 35 U.S.C. 154(b) by 412 days.

(21) Appl. No.: 16/786,374

(22) Filed: Feb. 10, 2020

(65) Prior Publication Data

US 2020/0316389 A1    Oct. 8, 2020

Related U.S. Application Data

(60) Provisional application No. 62/829,665, filed on Apr. 5, 2019.

(51) Int. Cl.
| | | |
|---|---|---|
| *A61N 1/05* | (2006.01) |
| *A61N 1/37* | (2006.01) |
| *A61N 1/375* | (2006.01) |
| *A61B 5/00* | (2006.01) |
| *A61N 1/378* | (2006.01) |
| *H02J 7/02* | (2016.01) |
| *H02J 50/10* | (2016.01) |
| *H05K 5/02* | (2006.01) |
| *H02J 7/00* | (2006.01) |
| *A61N 1/36* | (2006.01) |
| *H01R 13/52* | (2006.01) |

(52) U.S. Cl.
CPC .......... *A61N 1/3787* (2013.01); *H02J 7/0042* (2013.01); *H02J 7/02* (2013.01); *H02J 50/10* (2016.02); *H05K 5/0217* (2013.01); *A61N 1/36071* (2013.01); *H01R 13/5224* (2013.01)

(58) Field of Classification Search
None
See application file for complete search history.

(56) References Cited

U.S. PATENT DOCUMENTS

| | | |
|---|---|---|
| 6,817,905 B2 | 11/2004 | Zart et al. |
| 7,720,544 B2 | 5/2010 | Christman et al. |
| 8,929,986 B2 | 1/2015 | Parker et al. |
| 9,387,335 B2 | 7/2016 | Kane et al. |
| 10,758,735 B2 * | 9/2020 | Lim ................... A61N 1/37512 |
| 2017/0266451 A1 | 9/2017 | Lim et al. |
| 2020/0306547 A1 * | 10/2020 | Liu ....................... A61N 1/0573 |

* cited by examiner

*Primary Examiner* — Kenneth B Wells
(74) *Attorney, Agent, or Firm* — Laurence A. Greenberg; Werner H. Stemer; Ralph E. Locher

(57) ABSTRACT

A header for an implantable medical device includes at least an antenna and a receptacle for receiving a signal transmission line. Either one or a combination of the antenna and the receptacle are encased in a dielectric material. The dielectric material can be one of or include one of a polymer, a ceramic material, polyoxymethylene, polysulfone, polybutylene terephthalate. A medical device and a method for assembling a medical device are also provided.

14 Claims, 7 Drawing Sheets

MODULAR CONNECTOR HOUSING CONCEPT

CROSS-REFERENCE TO RELATED APPLICATION

This application claims the benefit, under 35 U.S.C. § 119(e), of Provisional Patent Application No. 62/829,665, filed Apr. 5, 2019; the prior application is herewith incorporated by reference in its entirety.

BACKGROUND OF THE INVENTION

Field of the Invention

The present invention relates to a header for a medical device, particularly for an implantable medical device, particularly for an implantable pulse generator. Further, the invention relates to a medical device and to a method for assembling a medical device.

Implantable medical devices such as stimulators to treat chronic pain often require a significant amount of energy for effective therapy delivery and therefore are equipped with rechargeable batteries. The recharging can be performed through transfer of electrical energy from an external coil to a charging coil located in the medical device. Since the transfer of energy generates heat in the medical device it is preferred to locate the receiving charging coil in the header of the medical device. A second key element for effective therapy is the ability for the patient to adjust therapy parameters using a wireless communication link e.g. using radio communication (e.g. Bluetooth).

Particularly, U.S. Pat. No. 8,929,986 B2 discloses a header including a communication antenna, a charging coil and receiving elements for electrode leads, wherein all components are at least partially encased in an epoxy volume.

Further, U.S. Pat. No. 6,817,905 B2 discloses a header manufactured in a two-step molding process, wherein a first core element with all electrical contacts and connectors is injection molded, and wherein in a second step the header is finished with an additional injection molding step.

Further, U.S. Pat. No. 9,387,335 B2 discloses a modular header including multiple pre-formed modules stacked on top of one another that are enclosed by a header shell.

Furthermore, U.S. Patent Application Publication No. 2017/0266451 A1 discloses a modular header-feedthrough including a pre-mounted header injection molded on a feedthrough flange, wherein the header-feedthrough is welded to the housing.

Finally, U.S. Pat. No. 7,720,544 B2 describes a header portion of an implantable device having an antenna which is molded in two compartments of different dielectric materials.

Typical difficulties that persist in headers of medical devices are the rather high complexity of the header due to the number of components disposed in a confined space, as well as limited options concerning optimization of electrical parameters of the header material with respect to communication, particularly due to direct contact with other components (e.g. lead connectors, charging coil etc.).

SUMMARY OF THE INVENTION

It is accordingly an object of the invention to provide a header for a medical device, a medical device and a method for assembling a medical device, which overcome the hereinafore-mentioned disadvantages of the heretofore-known devices and methods of this general type and which allow a simplification of the manufacturing process, as well as an optimized performance of a communication antenna and/or charging coil of the header.

With the foregoing and other objects in view there is provided, in accordance with the invention, a header for an implantable medical device, comprising at least an antenna, a third electronic component, and a receptacle for receiving a signal transmission line, either one or a combination of the antenna, the inductive charging coil and the receptacle being encased in a dielectric material, and the dielectric material can be one of or include one of: a polymer, a ceramic material, polyoxymethylene (POM), polysulfone (PSU), polybutylene terephthalate (PBT).

Preferably, according to an embodiment of the present invention, the third electronic component can be selected from the group of an inductive charging coil, a sensor element, a light emitting and/or receiving element or an electrode contact, and the third electronic element is encased in the dielectric material.

The signal transmission line can be an electrode lead including a plug for engaging with the receptacle and at least one electrode contact for contacting the tissue of a patient. Particularly, the electrode lead may include several (e.g. eight) electrode contacts.

According to an embodiment of the header, either one or a combination of the antenna, the inductive charging coil and the receptacle, are molded in the dielectric material.

Furthermore, according to an embodiment of the header, either one or a combination of the antenna, the inductive charging coil and the receptacle, are disposed in a compartment of the header, and the compartment is formed out of the dielectric material.

Further, while the dielectric material forming the compartment does not include an epoxy resin, the compartment can nonetheless be encased in an epoxy resin.

Further, in an embodiment, the header can include a further receptacle for receiving a further transmission line, the further receptacle can also be encased in the dielectric material, and/or molded in the dielectric material and/or disposed in the compartment (or further compartment).

The further signal transmission line can be a further electrode lead including a plug for engaging with the further receptacle and can include at least one electrode contact or several electrode contacts (particularly eight electrode contacts) for contacting tissue of a patient. Electrical stimulation can be applied to the tissue in the form of electrical current pulses through the electrode contacts. Particularly, the medical device can be an implantable medical device, particularly an implantable pulse generator (IPG) configured for stimulation of tissue, e.g. neurostimulation, particularly spinal cord stimulation (SCS).

Particularly, in an embodiment, the receptacle includes at least one electrical contact, particularly several (e.g. eight) electrical contacts. The respective electrical contact can be an annular electrical contact. Likewise, particularly, the further receptacle includes at least one electrical contact, particularly several (e.g. eight) electrical contacts. The respective electrical contact of the further receptacle can be an annular electrical contact. The electrical contacts of the receptacles are configured to make electrical contact with corresponding contacts of the respective signal transmission line (e.g. electrode lead) when the latter is received with its plug in the corresponding receptacle.

Furthermore, according to a preferred embodiment of the header, the header includes a further compartment formed of a further dielectric material being one of or including one of: a polymer, a ceramic material, an epoxy resin.

Particularly, according to an embodiment, the antenna is disposed in the compartment, or alternatively in the further compartment.

Furthermore, according to an embodiment, the receptacle is disposed in the further compartment or in the compartment. Furthermore, according to an embodiment, the further receptacle is disposed in the further compartment or in the compartment.

Further, according to an embodiment, the charging coil is disposed in the further compartment or in the compartment.

According to a preferred embodiment, the antenna is disposed in the compartment and the receptacle and particularly also the further receptacle is/are disposed in the further compartment. Furthermore, particularly, the charging coil can be disposed in the further compartment (or in the compartment), too.

According to a preferred alternative embodiment, the antenna is disposed in the compartment and the charging coil is disposed in the further compartment.

Furthermore, according to an embodiment, the compartment and the further compartment are connected to one another by at least one of: a form-locking connection, a force-locking connection, a material bond, an adhesive bond.

Particularly, in an embodiment the compartment includes at least one protrusion that engages with a guiding recess of the further compartment, for forming the form-locking connection. Alternatively, the further compartment may include at least one protrusion that engages with a guiding recess (e.g. a groove or aperture) of the compartment of the header.

Particularly, the header defines a thickness in a first direction, and the thickness is smaller than an extension of the header in a plane running perpendicular to the first direction.

Particularly, the at least one protrusion and the guiding recess are oriented in such a way that the at least one protrusion can be inserted into the guiding recess in a direction running perpendicular to the first direction or in a direction running parallel to the first direction.

Furthermore, according to an embodiment of the header, the further compartment includes a recess, the compartment is at least partially disposed in the recess of the further compartment, particularly in such a way that the compartment abuts with a first side against a first side of the further compartment, and particularly in such a way that the compartment abuts with a second side against a second side of the further compartment.

Particularly, in an embodiment, the two sides of the compartment (or of the further compartment) extend at an angle with respect to one another (e.g.) 90°, wherein particularly the at least one protrusion is disposed on the first side of the compartment or on the first side of the further compartment. Correspondingly, the guiding recess is disposed on the first side of the further compartment or on the first side of the compartment.

Particularly, the compartment includes a further protrusion that engages with a further guiding recess of the further compartment. Alternatively, the further compartment can include a further protrusion that engages with a further guiding recess (e.g. a groove or aperture) of the compartment. Particularly, the further protrusion can be disposed on the second side of the compartment (in this case, the further guiding recess can be disposed on the second side of the further compartment) or on the second side of the further compartment (in this case the further guiding recess can be disposed on the second side of the compartment).

With the objects of the invention in view, there is also provided a medical device comprising a header according to the present invention and a housing (also denoted as a can) connected to the header, the housing encapsulating a battery and/or an electronic module of the medical device. Particularly, the battery is connected to the electronic module.

Further, according to an embodiment of the medical device, the medical device is an implantable medical device, particularly an implantable pulse generator (IPG), wherein particularly the IPG is configured for stimulating tissue, e.g. neurostimulation, particularly for spinal cord stimulation (SCS).

Furthermore, in an embodiment of the medical device, the antenna, the inductive charging coil, and the receptacle (particularly also the further receptacle), are each electrically connected to the electronic module through electrical feedthroughs.

With the objects of the invention in view, there is furthermore provided a method for assembling a medical device, particularly a medical device according to the present invention, comprising the steps of:

placing an electronic module in a housing and connecting the electronic module to electrical feedthroughs protruding out of the housing, closing the housing (e.g. by welding), connecting at least one electronic component to feedthroughs of the housing, molding a first compartment (e.g. the further compartment described above) to the housing to encase the at least one electronic component in the first compartment, wherein the first compartment is formed out of a first dielectric material, connecting a second compartment formed out of a second dielectric material to the first compartment and/or to the housing, and connecting at least one electronic component encased in the second compartment to feedthroughs of the housing.

According to an embodiment of the method, the at least one electronic component encased by the first compartment (e.g. further compartment) is a receptacle for a signal transmission line (see also above).

Further, according to a further embodiment of the method, the at least one electronic component of the second compartment is an antenna (e.g. for conducting communication with the medical device) or a charging coil.

Furthermore, according to an embodiment of the method, the first dielectric material or the second dielectric material does not include an epoxy resin. Suitable dielectric materials for the first compartment (e.g. the further compartment described above) and the second compartment (e.g. the compartment described above) are stated above.

Particularly, in an embodiment of the method, before closing the housing, a battery is also disposed in the housing. The battery is connected to the electronic module. The electronic module and the battery can be connected to one another before placing the electronic module and the battery in the housing. The electronic module and the battery can also be connected to one another when already disposed in the housing.

Other features which are considered as characteristic for the invention are set forth in the appended claims.

Although the invention is illustrated and described herein as embodied in a header for a medical device, a medical device and a method for assembling a medical device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
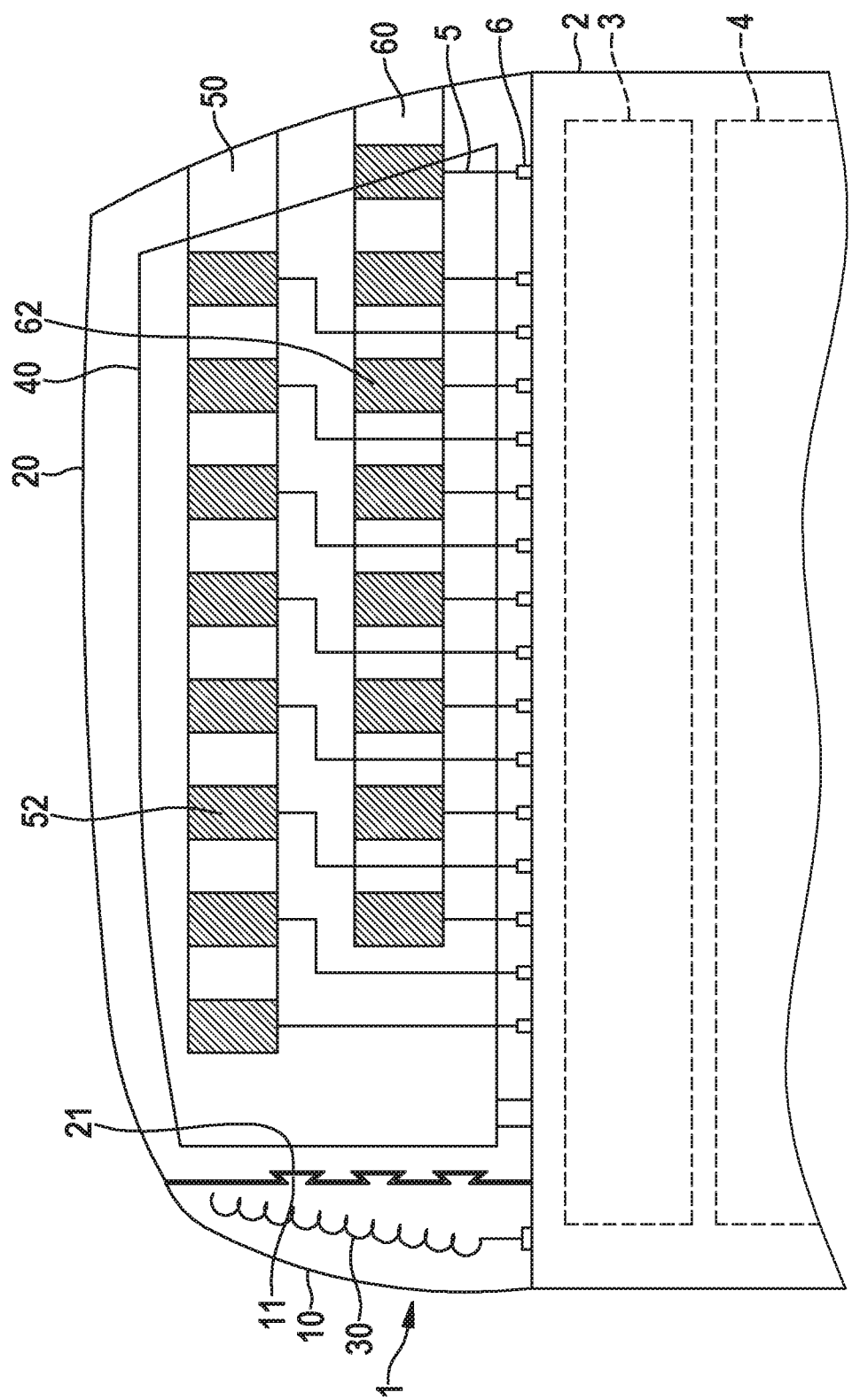
FIG. 1 is a fragmentary, diagrammatic, cross-sectional view of an embodiment of a header according to the present invention, wherein the header includes two compartments formed out of dielectric materials for holding components of the header.

Referring now to the figures of the drawings in detail and first, particularly, to FIG. 1 thereof, there is seen an embodiment of a header 1 according to the present invention. Particularly, the header 1 can form part of a medical device according to the present invention, particularly an implantable pulse generator including a housing 2 connected to the header 1. The housing 2 can enclose all of the electronics necessary to perform therapy and/or sensing. The electronics may include signal generators, transceiver units for communication, and sensing circuits, typically disposed on an electronic module 3. The electronic module 3 is connected on one side to a preferably rechargeable battery 4. It also may contain a charging circuit for charging the battery 4.

The other connections of the electronic module 3 are typically going to the header 1 through feedthroughs 6 and suitable electrical conductors 5.

According to the present invention the header 1 includes at least an antenna 30, and/or an inductive charging coil 40, and at least one receptacle 50 for receiving a signal transmission line, particularly in the form of an electrode lead, which may include a plug 51 to engage with the receptacle 50. Preferably, either one of or a combination of the antenna 30, the inductive charging coil 40, the receptacle 50, are encased in a dielectric material that does not include an epoxy resin.

According to a preferred embodiment the header 1 includes at least a compartment 10 and a further compartment 20 mated together, for example with an anchoring device (e.g. a latching or positive, form-locking connection) 11, 21. Alternatively, the two compartments 10, 20 can be adhered or molded together.

As indicated in FIG. 1, in this preferred embodiment, the compartment 10 can encase the antenna 30 that is configured for radio communication of the medical device with a further device. Furthermore, the further compartment 20 preferably encases at least one receptacle 50 for receiving a signal transmission like an implantable electrode lead. Multiple electrical contacts 52 are situated in the receptacle 50. Each of these contacts 52 can be electrically connected through a conductor 5, particularly a connecting wire 5, to an electronic interface 6 (also known as the feedthrough 6) on the housing 2 in order to transmit therapy signals from the signal generator to a tissue to be stimulated, and/or to collect physiological signals to be evaluated.

Particularly, the communication antenna 30 can be configured for use with the commonly known bi-directional communication techniques (e.g. BLE, MICS, . . . ). The antenna 30 is preferably electrically connected to a transceiver unit through one or two connecting wires 5 and electronic interfaces/feedthroughs 6.

Alternatively or additionally to the antenna 30, the coil 40 with multiple turns for communication and/or charging the rechargeable battery 4 can be encased by the compartment 10. In the latter case the charging coil 40 is preferably connected to the charging circuit in the electronics module 3 in the housing 2.

According to FIG. 1, the further compartment 20 may additionally or alternatively include at least one further receptacle 60 having multiple electrical contacts 62 for making an electrical connection to a further signal transmission line/further electrode in the same fashion as the receptacle 50. Preferably all of the elements 30, 40, 50, 60 are connected to the electronics module 3 in the electronics housing 2 through the connecting wires 5 and the electronic interfaces/feedthroughs 6.

Further, in the embodiment shown in FIG. 1, the further compartment 20 preferably includes the charging coil 40.

Preferably, the compartment 10 is formed out of the dielectric material that does not include an epoxy resin. This dielectric material can be one of or include one of: a polymer, a ceramic material, polyoxymethylene (POM), polysulfone (PSU), polybutylene terephthalate (PBT).

Preferably, the further compartment 20 is formed of a further dielectric material that is preferably different from the dielectric material of the compartment 10, wherein the further dielectric material particularly includes one of: a polymer, a ceramic material, an epoxy resin.

However, according to an embodiment, the dielectric materials for the compartments 10, 20 may also be interchanged.

Figure 3:
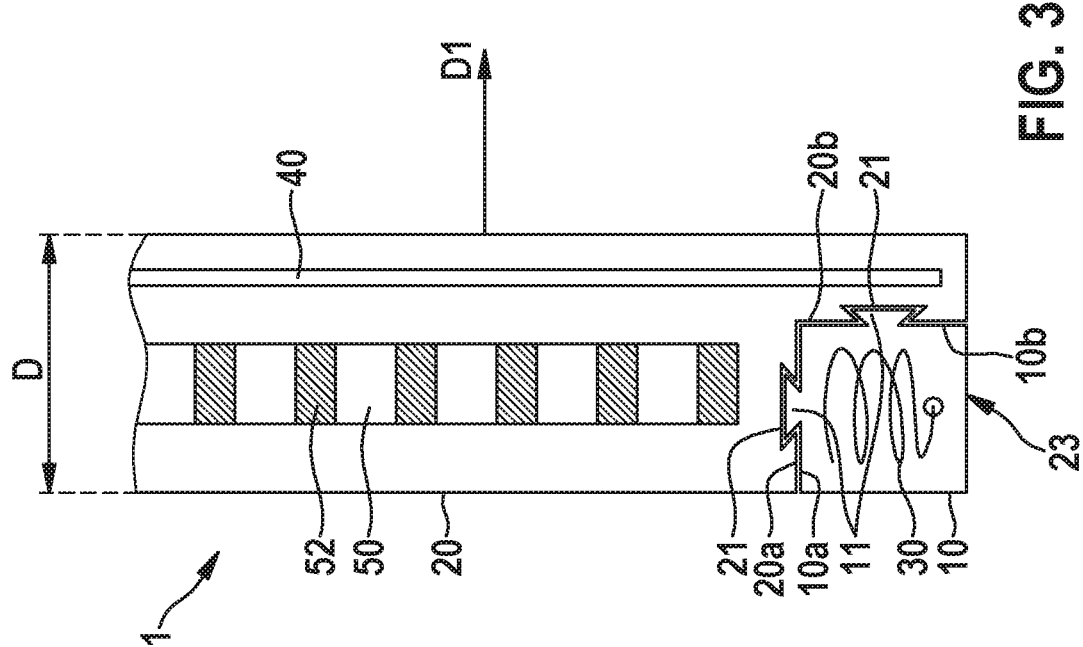
FIG. 3 is a cross-sectional view of a further embodiment of a header according to the present invention, wherein the header includes two compartments formed out of dielectric materials for holding components of the header.
Figure 2:
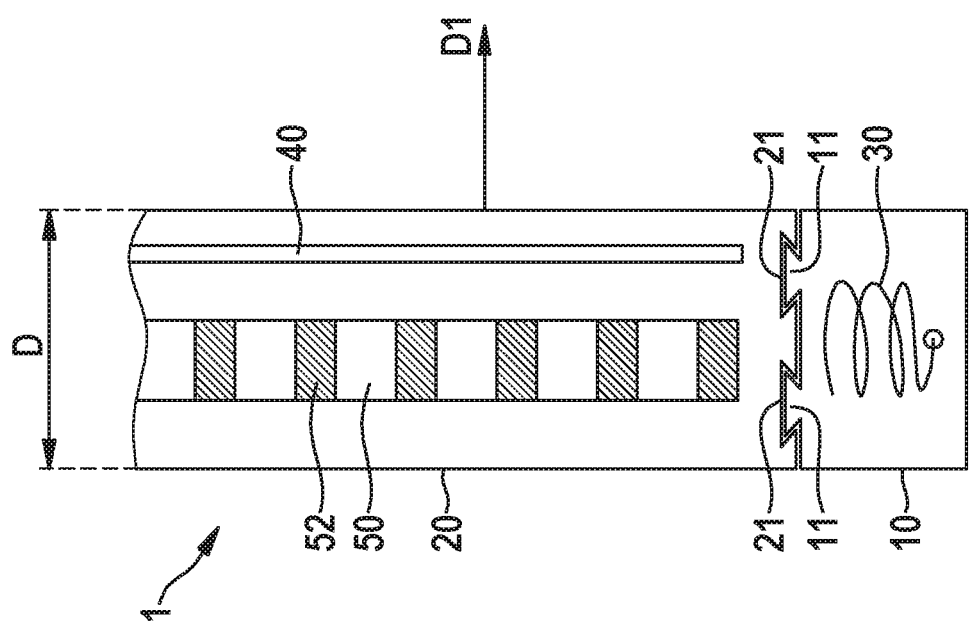
FIG. 2 is a cross-sectional view of a further embodiment of a header according to the present invention, wherein the header includes two compartments formed out of dielectric materials for holding components of the header.

While FIG. 1 shows a variant in which the connection between the two compartments includes protrusions 11 and guiding recesses 21 extending in a first direction D1 in which the header includes its smallest dimension (i.e. thickness D), FIGS. 2 and 3 show embodiments in which the orientation of these protrusions/guiding recesses preferably extend perpendicular to the first direction D1.

Particularly, FIG. 2 shows a top view onto the header 1, according to which an attachment is established between the two compartments 10, 20 by anchoring devices, which are used to mate the compartments 10, 20 securely in place. In a preferred embodiment, the compartment 10 includes at least one, particularly two protrusions 11 which may form anchors and are configured to engage with corresponding guiding recesses 21 formed in the further compartment 20. Thus, the compartment 10 may be inserted from the top of the header 1 to slide downwards in place. In other embodiments the at least one guiding recess may allow the insertion in a lateral direction, i.e. parallel to the first direction D1. In further embodiments, the compartment 10 may include at least one guiding recess and the further compartment 20 may include at least one mating protrusion/anchor. Other attachment methods are possible, like snap-fit connections.

In an alternative preferred embodiment, shown in FIG. 3, the further compartment 20 includes a recess 23, in which the compartment 10 can be inserted. In this case, the volume of the further compartment encases the compartment partially, at least on two sides 10a, 10b of the compartment. The two sides 10a, 10b particularly extend at an angle, e.g. 90°. Particularly a protrusion 11 can protrude from each side 10a, 10b of the compartment 10, wherein the respective protrusion engages with a corresponding guiding recess 21 of the further compartment 20. Each guiding recess 21 can be formed on a side 20a, 20b of the further compartment 20 that butts against an associated side 10a, 10b of the compartment 10.

Additionally, or alternatively, the compartments 10, 20 can be attached to each other by adhering or molding both compartments 10, 20 together.

In a preferred embodiment, the further compartment 20 is attached to the electronics housing, before the compartment 10 is attached to the further compartment 20. In this embodiment, a possible assembling process may include the steps of:
- Electrically connecting one connection wire 5 to each of the multiple electrical contacts 52, 62 in the at least one receptacle 50, 60 (e.g. by welding). Optionally, at least one further additional electric component may be disposed besides the at least one receptacle and electrically connecting connection wires.
- Electrically connecting each of the connection wires 5 with one electronic interface (e.g. feedthrough 6) at the housing 2.
- Placing the wired electronics housing 2 in a mold.
- Molding the further compartment 20 to the housing 2.
- Attaching the compartment 10 to the further compartment.
- Electrically connecting the electronic component (e.g. antenna 30 and/or charging coil 40) in the compartment 10 with electronic interfaces (e.g. feedthroughs) 6; and
- Optionally, applying additional molding or bonding processes.

Figure 4:
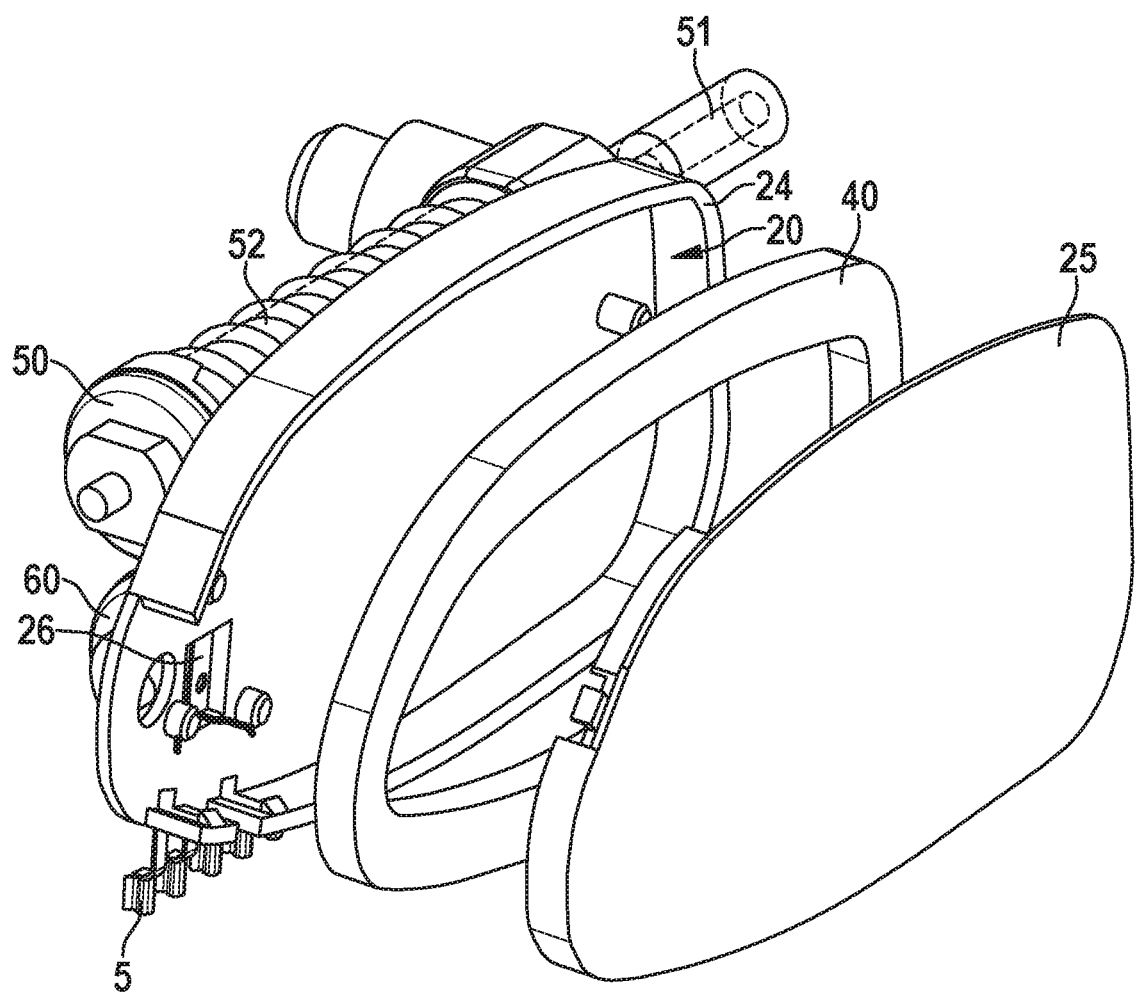
FIG. 4 is an exploded, perspective view of a further embodiment of a header according to the present invention, wherein the header includes a compartment formed out of dielectric material for holding a charging coil.
Figure 5:
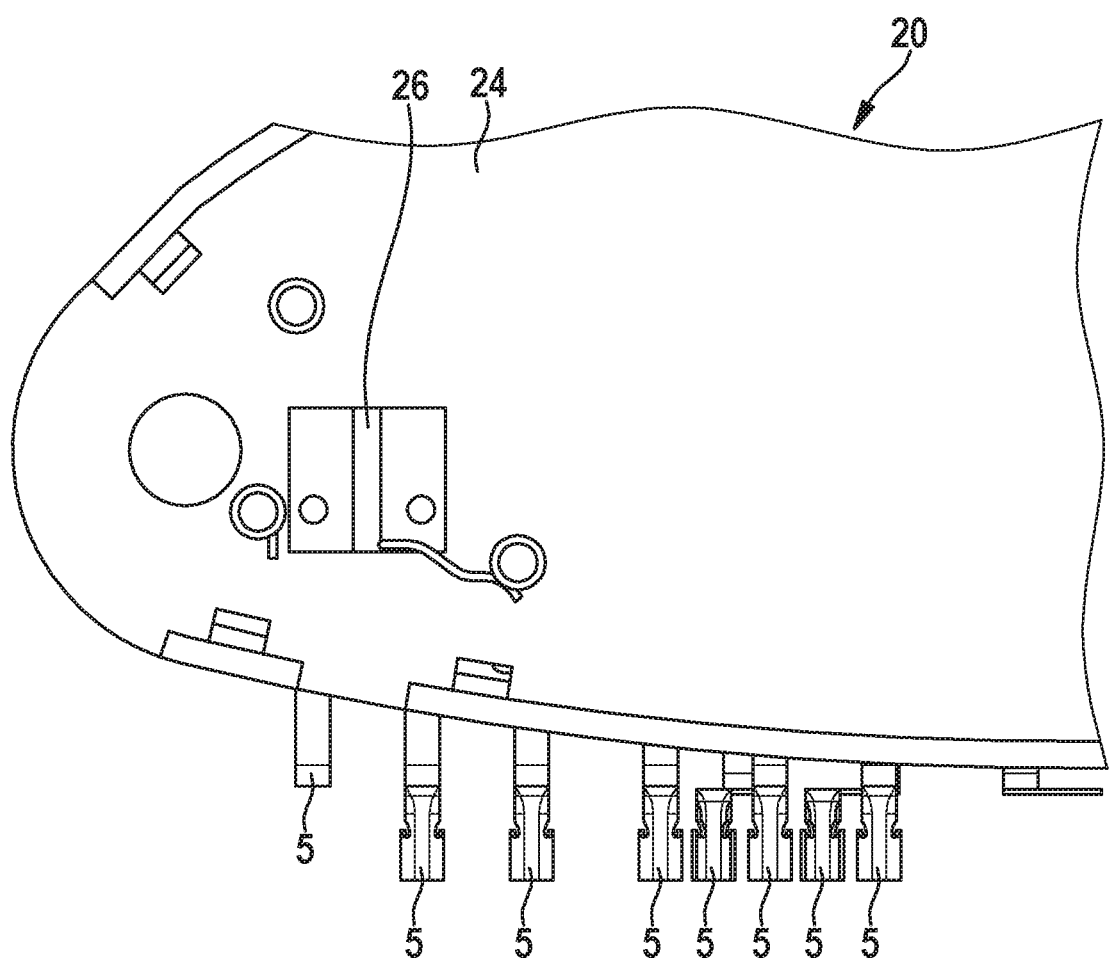
FIG. 5 is a bottom plan view of the compartment of the header shown in FIG. 4.
Figure 8:
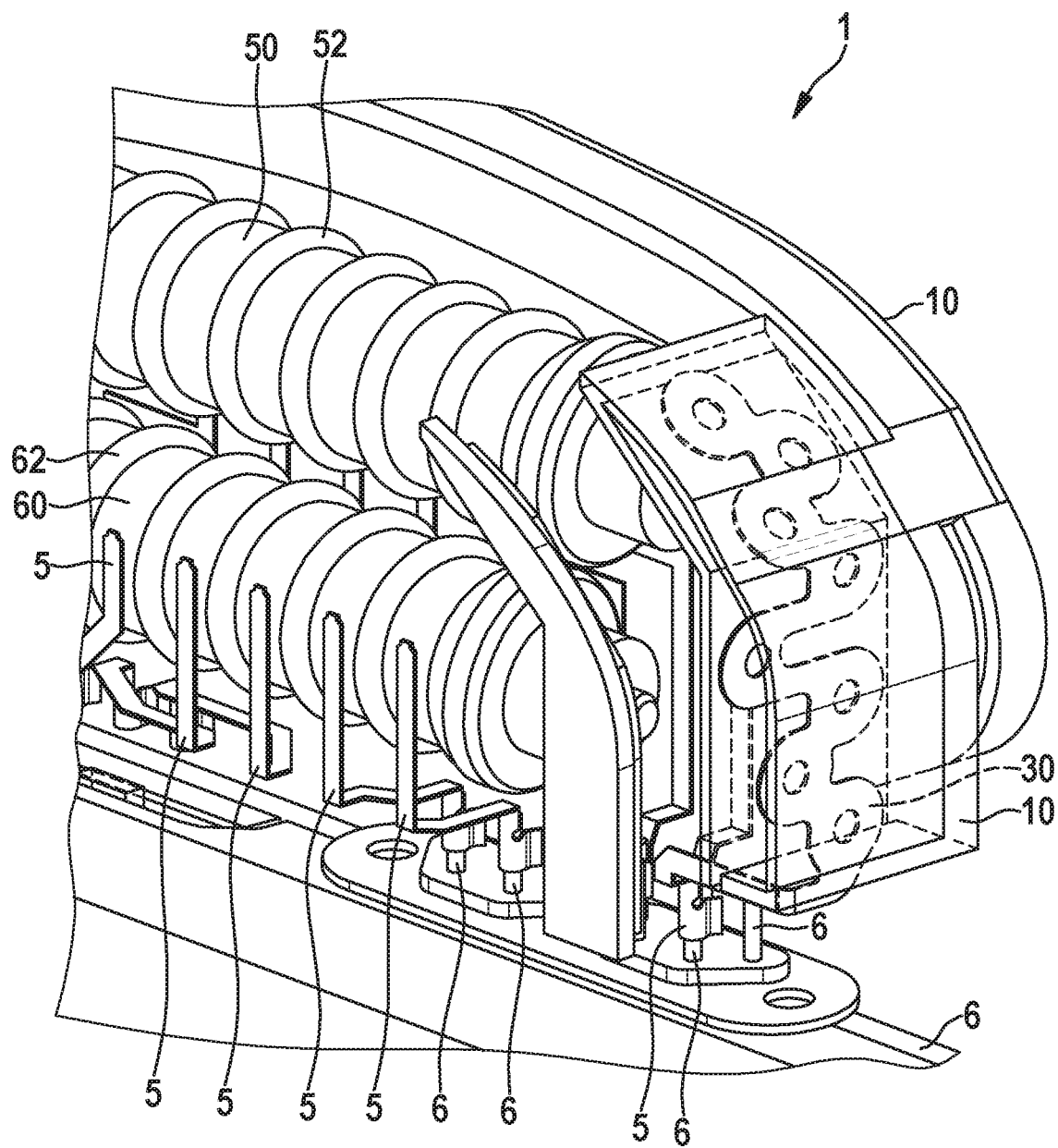
FIG. 8 is a fragmentary, perspective view of a variant of the header according to FIGS. 4 to 7, wherein in addition an antenna is held by the compartment including the charging coil.

FIG. 4 shows in conjunction with FIG. 5 a further embodiment of a header 1 according to the present invention, wherein in this case only the compartment 10 is shown which encases a charging coil 40 for charging a battery 4 of the medical device. The compartment can include a bottom 24 and a lid 25 to enclose the charging coil 40. Furthermore, the bottom 24 can include a through hole 26 so that the charging coil can be electrically connected to conductors 5 connected to the feedthroughs 6 of the housing 2 of the medical device (see FIG. 8).

Figure 6:
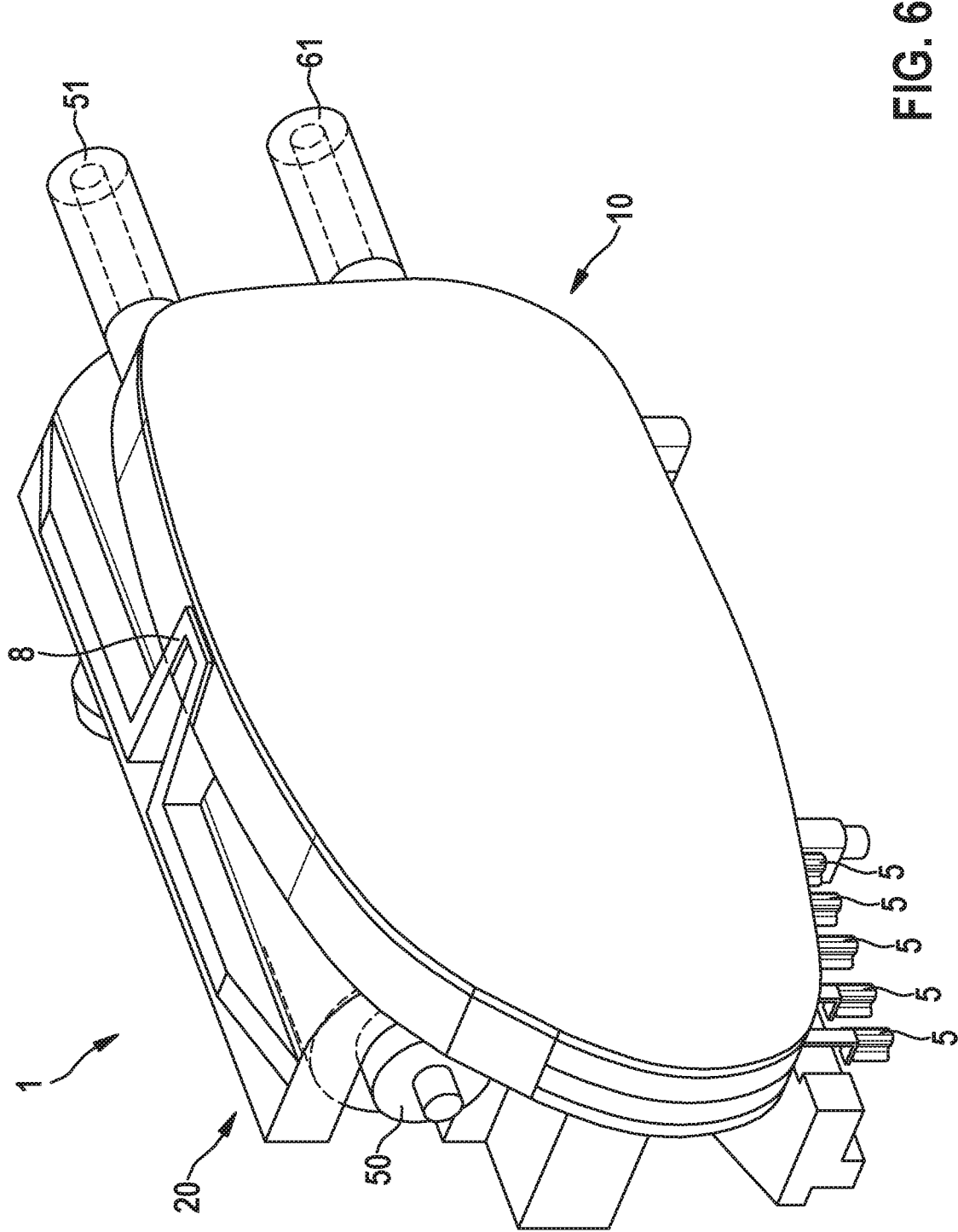
FIG. 6 is a perspective view of the header shown in FIGS. 4 and 5.
Figure 7:
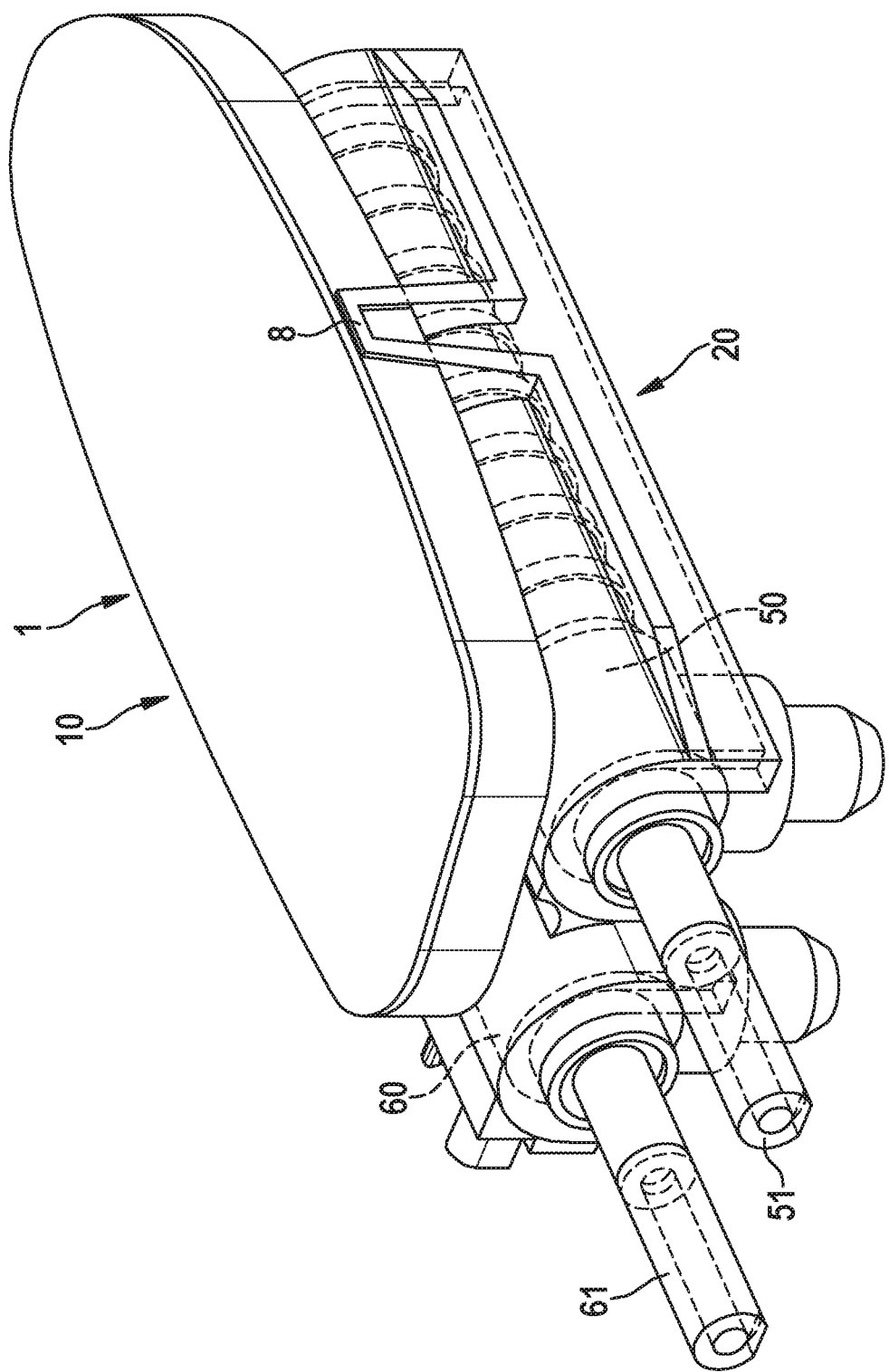
FIG. 7 is a further perspective view of the header shown in FIGS. 4 to 6.

Furthermore, FIGS. 6 and 7 also show the further compartment 20 which encases the at least one receptacle 50, 60 particularly the two receptacles 50, 60 for making connection to signal transmission lines/electrode leads.

Particularly, as described above, the further compartment 20 can first be molded to the housing 2 to encase the receptacle(s) 50, 60 in the dielectric material of the further compartment. The further compartment 20 can include one or multiple latching devices 8 (e.g. in the form of one or more latching wings 8) to connect the compartment 10 to the further compartment 20 after molding of the further compartment 20 to the housing 2.

Furthermore, alternatively or in addition, the compartment 10 may house the communication antenna 30 of the header 1.

The compartment 10 including the charging coil 40 and/or the antenna 30 is preferably formed out of a dielectric material that does not include an epoxy resin. The further compartments may be formed out of an epoxy resin. Particularly, the materials stated above can be used for the compartment 10 and the further compartment 20 of the header.

Advantageously, particularly regarding the embodiment shown in FIG. 2, the invention provides a greater separation distance between the communication antenna 30 in the compartment 10 and other (e.g. metallic) components in the further compartment 20, resulting in a better/more reliable communication performance. The greater separation distance is due to the fact that the communication antenna 30 is fully supported by the material of the compartment 10, particularly with no interface to supporting structures of the further compartment 20 of the header 1. In addition, the electrical properties of the dielectric material of the compartment 10 can be adjusted to optimize the transmission performance of the communication antenna 30. Furthermore, the structure allows for better control of the location of the communication antenna 30 with respect to the outer surface of the compartment 10, which improves the efficacy of the manufacturing process.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

The invention claimed is:

1. A header for an implantable medical device, the header comprising:
    an antenna;
    a receptacle for receiving a signal transmission line; and
    a dielectric material encasing said antenna or said receptacle or a combination of said antenna and said receptacle;
    a compartment formed of said dielectric material, said antenna or said receptacle being disposed in said compartment;
    said dielectric material being one of or including one of: a polymer, a ceramic material, polyoxymethylene, polysulfone or polybutylene terephthalate.

2. The header according to claim 1, which further comprises an electronic component selected from the group consisting of an inductive charging coil, a sensor element, a light emitting or receiving element and an electrode contact, said third electronic element being encased in said dielectric material.

3. The header according to claim 2, wherein one or a combination of said antenna, said third electronic component or said receptacle are molded in said dielectric material.

4. The header according to claim 2, wherein said third electronic component is disposed in said compartment.

5. The header according to claim 4, which further comprises a further compartment formed of a further dielectric material, said further dielectric material including one of: a polymer, a ceramic material or an epoxy resin.

6. The header according to claim 5, wherein one or a combination of said antenna, said receptacle or said third electronic component is disposed in said further compartment.

7. The header according to claim 6, wherein said compartment and said further compartment are connected to one another by at least one of: a form-locking connection, a force-locking connection, a material bond or an adhesive bond.

8. The header according to claim 6, wherein:
one of said compartment or said further compartment includes at least one protrusion;
another of said compartment or said further compartment includes at least one guiding recess; and
each protrusion engages in a respective guiding recess.

9. The header according to claim 5, wherein said further compartment includes a recess, and said compartment is disposed in said recess of said further compartment.

10. A medical device, comprising:
at least one of a battery or an electronic module of the medical device;
a header according to claim 1; and
a housing connected to said header, said housing encapsulating said at least one of said battery or said electronic module.

11. The medical device according to claim 10, which further comprises an inductive charging coil, and electrical feedthroughs electrically connecting each of said antenna, said inductive charging coil and said receptacle to said electronic module.

12. A method for assembling a medical device including a header and a housing, the method comprising the following steps:
placing an electronic module in the housing and connecting the electronic module to electrical feedthroughs protruding out of the housing;
closing the housing;
connecting at least one electrical component to the housing;
molding a first compartment of the header to the housing to encase the at least one electrical component in the first compartment;
connecting a second compartment of the header to at least one of the first compartment or the housing; and
connecting at least one electronic component encased in the second compartment to the feedthroughs of the housing.

13. The method according to claim 12, which further comprises providing the electrical component as a receptacle for receiving a signal transmission line.

14. The method according to claim 12, which further comprises providing the electronic component as one or a combination of an antenna, an inductive charging coil, a sensor element, a light emitting or receiving element or an electrode contact.

* * * * *